US006823209B2

(12) United States Patent
Olson et al.

(10) Patent No.: US 6,823,209 B2
(45) Date of Patent: Nov. 23, 2004

(54) ELECTROCARDIOGRAM FILTER

(75) Inventors: Dana J. Olson, Kirkland, WA (US); Scott O. Schweizer, Snohomish, WA (US); Tyler R. Hart, Kenmore, WA (US); David Van Ess, Arlington, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 320 days.

(21) Appl. No.: 09/982,111

(22) Filed: Oct. 19, 2001

(65) Prior Publication Data

US 2003/0078510 A1 Apr. 24, 2003

(51) Int. Cl.[7] ............................................. A61B 5/0402
(52) U.S. Cl. ...................................... 600/510; 600/509
(58) Field of Search ................................. 600/509–510, 600/513, 529; 607/9, 27–28

(56) References Cited

U.S. PATENT DOCUMENTS

| | | | |
|---|---|---|---|
| 3,547,108 A | 12/1970 | Seiffert | 600/525 |
| 3,865,101 A | 2/1975 | Saper et al. | 600/508 |
| 4,106,494 A | 8/1978 | McEachern | 600/508 |
| 4,419,998 A | 12/1983 | Heath | 600/391 |
| 4,494,552 A | 1/1985 | Heath | 600/509 |
| 4,658,831 A | 4/1987 | Reinhard et al. | 600/510 |
| 4,919,144 A | 4/1990 | Vandehey | 600/518 |
| 4,974,600 A | 12/1990 | Reyes | 600/509 |
| 5,105,821 A | 4/1992 | Reyes | 600/508 |
| 5,231,990 A | 8/1993 | Gauglitz | 600/510 |
| 5,301,677 A | 4/1994 | Hsung | 600/518 |
| 5,402,795 A * | 4/1995 | Reichl | 600/508 |
| 5,421,342 A | 6/1995 | Mortara | 600/508 |
| 5,458,124 A | 10/1995 | Stanko et al. | 600/509 |
| 5,511,553 A | 4/1996 | Segalowitz | 600/508 |
| 5,660,184 A * | 8/1997 | Donehoo et al. | 600/509 |
| 5,711,304 A | 1/1998 | Dower | 600/523 |
| 5,778,881 A * | 7/1998 | Sun et al. | 600/509 |
| 5,792,207 A * | 8/1998 | Dietrich | 607/32 |
| 6,246,907 B1 | 6/2001 | Lin et al. | 607/5 |
| 6,275,734 B1 * | 8/2001 | McClure et al. | 607/27 |
| 2003/0073915 A1 * | 4/2003 | McLeod et al. | 600/509 |

\* cited by examiner

Primary Examiner—Carl Layno
(74) Attorney, Agent, or Firm—Shumaker & Sieffert, P.A.

(57) ABSTRACT

The invention presents techniques for identifying signals detected by electrodes on the body of a patient as part of a reading of the patient's electrocardiogram. A signal processor digitally filters the signal from the body, resulting in an electrocardiogram signal and a signal that identifies the presence and timing of signals from a pacemaker in the body. Other signals, such as a signal that reflects the quality of the electrical connection of the electrode to the body, may also be obtained by digital filtering.

26 Claims, 5 Drawing Sheets

ELECTROCARDIOGRAM FILTER

FIELD

The invention relates to medical devices for treating cardiac conditions, and more particularly, to medical devices using an electrocardiogram.

BACKGROUND

An electrocardiogram (ECG) is a recording of the electrical activity of the heart conducted through the body of a patient. The ECG records the difference in potential between two or more electrodes placed upon the body of the patient. In some circumstances, several electrodes are placed on the patient. In other circumstances, such as an emergency situation in which sudden cardiac arrest is suspected, fewer electrodes may be used.

An automated external defibrillator (AED) is an example of a device that may employ two electrodes to record an ECG. An operator such as an emergency medical technician attaches one defibrillation electrode to the upper right side of the chest of a patient who is suspected of experiencing cardiac distress. The operator attaches another defibrillation electrode to the lower left side of the chest. The AED generally measures the patient's ECG automatically, using the defibrillation electrodes as sensors. The AED also assesses whether a defibrillation shock is indicated based upon the ECG, and charges a storage element in preparation for giving the shock. When a shock is indicated, the AED may cue the operator to administer the shock, or the AED may administer the shock automatically. The patient receives the shock through the same electrodes.

The treatment provided by the AED to the patient depends upon the ECG signal. One factor that may influence the clarity of the signal is the quality of the connection of the electrodes to the patient. In the case of a patient with a hairy chest, for example, an electrode placed on the chest may lose contact with the patient's skin, resulting in a poor electrical connection.

In addition, the electrical activity embodied in the ECG signal may be influenced by factors such as a pacemaker. A patient having an apparently abnormal heart rhythm may actually be having the heart rhythm controlled by a pacemaker. In such a case, the AED should recognize the presence of pacing, and may adjust its analysis of the ECG signal.

SUMMARY

The invention is directed to techniques for identifying and/or monitoring signals of interest detected by electrodes on the body of a patient. One of the signals is the patient's electrocardiogram. Other signals include a signal that identifies the presence and timing of signals from a pacemaker in the body, and a signal that reflects the quality of the electrical connection of the electrode to the body. These signals are received superimposed upon one another, and are separated with digital filters.

In an exemplary implementation, the electrical signal from the body is passed through an anti-aliasing filter and is then converted to a digital signal. A digital signal processor digitally filters the digital signal to monitor the ECG signal, identify pacemaker signals and assess the quality of the electrical connection. In addition to generating these signals with digital filtering, the digital signal processor may analyze the signals. In addition, the digital signal processor may control a subsystem such as defibrillation circuitry, based upon the analysis.

In one embodiment, the invention presents a device comprising a first digital filter that receives a digital signal representative of a signal from a body and generates a pacemaker signal as a function of pacing pulses supplied by a pacemaker and a second digital filter that receives the digital signal and generates an electrocardiogram signal. The device may further include a third digital filter that receives the digital signal and generates a signal indicative of the quality of the electrical connection of an electrode to the body. This embodiment may be employed in many environments, including an electrocardiogram system in a hospital or an AED out in the field.

In another embodiment, the invention presents a method comprising digitally filtering an electrical signal representative of a signal from a body to generate a pacemaker signal as a function of pacing pulses supplied by a pacemaker and digitally filtering the electrical signal to generate an electrocardiogram signal. The method may include commencing a defibrillation sequence, depending upon the analysis.

In a further embodiment, the invention presents a device that includes an analog-to-digital converter and a processor. The processor performs the digital filtering operations. The processor may further perform the analysis of the signals obtained by digital filtering.

Digital filtering brings about many benefits. For example, digital filters are smaller than conventional analog filters, thus saving space and weight. Digital filters are easily programmed and easily adjusted. Digital filters are generally more reliable than their analog counterparts. Digital filters may also be inexpensive.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
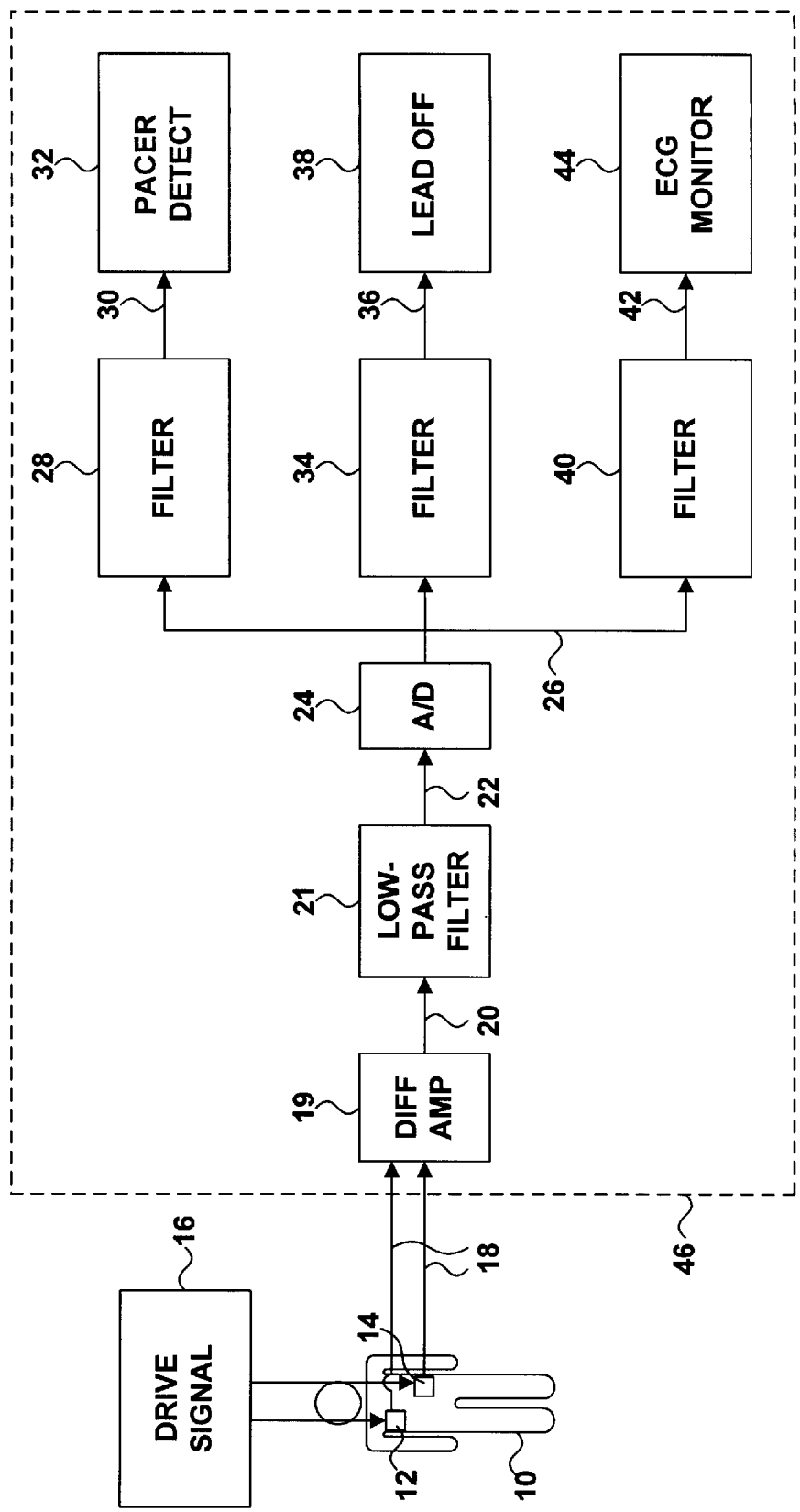
FIG. 1 is a functional block diagram illustrating an embodiment of the invention.

FIG. 1 shows a patient 10 that receives electrodes 12, 14. Electrodes 12, 14 conduct electrical signals on the skin of patient 10. A signal processor 46 receives raw signals 18 from patient 10. Raw signals 18 represent the potential difference between electrodes 12 and 14, and include several superimposed electrical signals. Some of the electrical signals in raw signals 18 are of particular interest. Signal processor 46 discards some signals, and separates the signals of particular interest, specifically signals 30, 36 and 42, from each other.

One signal of interest in raw signals 18 is ECG signal 42, i.e., the electrical activity of the heart sensed at the surface of the body of patient 10. Most ECG signals, whether normal or abnormal, include frequency components in the range of zero to 150 Hz. ECG signal 42 may be displayed, stored, printed, transmitted and/or processed further by ECG monitor 44.

ECG signal 42 provides useful information about the rate and rhythm of the heart. ECG monitor 44 evaluates the information in ECG signal 42. In particular, ECG monitor 44 assesses whether the heart of patient 10 is showing an abnormal rate or rhythm. When the rate or rhythm is abnormal, ECG monitor 44 may classify the abnormality, such as fibrillation, tachycardia or heart block. In the case of an AED, analysis of ECG signal 42 precedes a determination as to whether patient 10 exhibits a shockable rhythm.

A second useful signal that may be included in raw signals 18 is pacemaker signal 30, which may be displayed and/or processed by pacer detection system 32. If patient 10 has an internal or external pacemaker, raw signals 18 include pacemaker signal 30, usually in the form of one or more voltage spikes of short duration, typically between 0.5 and 2.0 milliseconds. A typical spike includes frequency components in the range of 300 to 3000 Hz. The spike is caused by an implanted pacemaker that stimulates the heart. If patient 10 does not have an active implanted pacemaker, the spike will not be present.

Pacer detection system 32, therefore, identifies the presence of a pacemaker in the body of patient 10. Pacer detection system 32 further analyses the timing of the spikes, which is directly related to the timing of the pacing pulses received by patient 10. The timing of pacing pulses may be useful, for example, in the analysis of ECG signal 42.

In addition, raw signals 18 include a component due to a drive signal 16. As will be described below, drive signal 16 is used to assess the quality of the connection of one or more electrodes to patient 10. Drive signal 16 is supplied to electrodes 12 and 14 from outside the body of patient 10. As will be described below, drive signal 16 may be generated under the control of a digital signal processor (not shown in FIG. 1) in signal processor 46. In one embodiment, drive signal 16 is a sinusoidal current of known magnitude, phase and frequency. A drive signal may have a frequency of about 300 Hz.

The voltage of lead off signal 36, detected by lead off detector 38, reflects the strength of drive signal 16 and the impedance of the patient. The purpose of applying drive signal 16 to electrodes 12 and 14 and sensing lead off signal 36 is to measure the quality of the connection of electrodes 12 and 14. The magnitude of lead off signal 36 is a function of the quality of the connection. A large voltage sensed by lead off detector 38, for example, indicates an increase in impedance between electrodes 12 and 14, which in turn indicates that at least one of electrodes 12 and 14 is poorly connected to patient 10. Lead off detector 38 may notify the operator of the poor connection, and the operator may correct the problem.

Signal processor 46 receives raw signals 18 and generates pacemaker signal 30, lead off signal 36 and ECG signal 42. Signal processor 46 includes difference amplifier 19, which generates a signal 20 as a function of the potential difference between electrodes 12 and 14. Analog low-pass filter 21 receives difference signal 20 and acts as an anti-aliasing filter by removing high frequency components from signal 20. In one embodiment, low-pass filter 21 comprises a combination Butterworth and Bessel filter, with a bandwidth of 3000 Hz, unity gain, and linear phase shift of the frequency components.

Low-pass filter 21 passes filtered signal 22 to analog-to-digital (A/D) converter 24. In one embodiment, A/D converter 24 is a 16-bit converter operating at a sampling rate of 25,000 samples per second, and is configured to handle signed data. Other sampling rates may be employed, but the sampling rate should be sufficiently high to sample the desired signals passed by low-pass filter 21 and to avoid aliasing of noise.

A/D converter 24 passes digital signal 26 to digital filters 28, 34 and 40, which extract signals of interest 30, 36 and 42. Digital signal 26 is representative of signals from the body of patient 10. In one embodiment, digital filter 28 passes frequencies above 300 Hz, and is implemented as a fourth-order Butterworth filter with an infinite impulse response (IIR). Digital filter 34 is implemented as a fourth-order IIR filter with a narrow passband at 300 Hz. Digital filter 40 passes frequencies below 150 Hz and is implemented as a filter with a finite impulse response.

Figure 2:
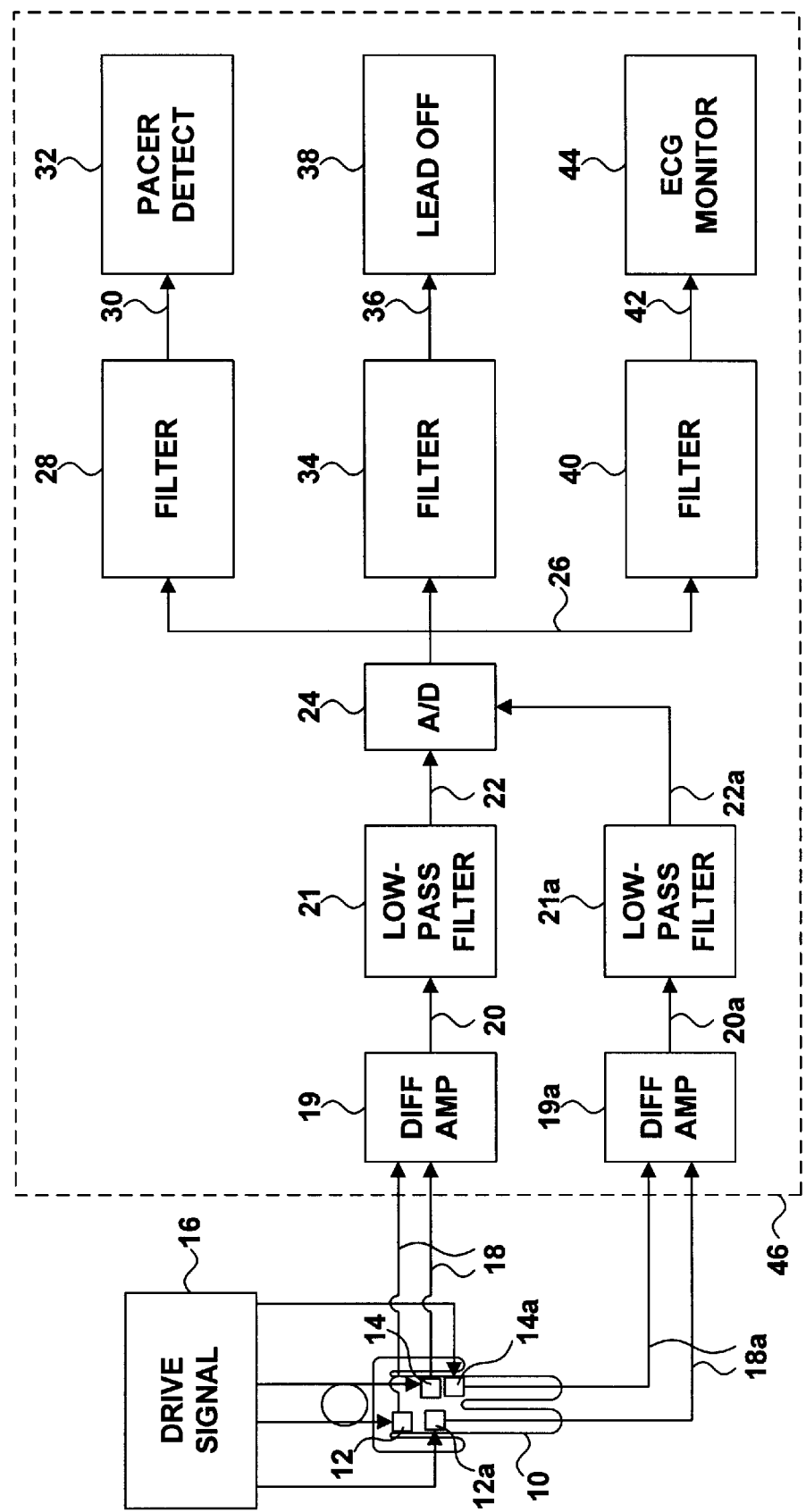
FIG. 2 is a functional block diagram illustrating an embodiment of the invention that includes two channels.

FIG. 2 demonstrates an embodiment of the invention with more than two electrodes. FIG. 2 is like FIG. 1 except that FIG. 2 shows a second processing channel. In addition to electrodes 12 and 14, electrodes 12*a* and 14*a* are in contact with the skin of patient 10. Raw signals 18*a* from electrodes 12*a* and 14*a* are received by a second difference amplifier 19*a* in signal processor 46. Second difference amplifier 19*a* generates a signal 20*a* as a function of the potential difference between electrodes 12*a* and 14*a*, which is received by a second anti-aliasing filter 21*a*. A second filtered signal 22*a* is passed to A/D converter 24.

In this embodiment, A/D converter 24 processes multiple data channels. A 16-bit converter operating at a sampling rate of 50,000 samples per second can sample each filtered signal 22, 22*a* at 25,000 samples per second. The resulting digital signal 26 may include digital data from both channels. Data from any particular channel can be recovered by techniques such as demultiplexing.

Furthermore, the invention is not limited to separate pairs of electrodes. For example, patient 10 may receive three electrodes, consisting of electrodes 12, 14 and a third electrode (not shown in FIG. 2). The potential difference between electrodes 12, 14 may be processed via one channel, the potential difference between electrode 12 and the third electrode may be processed via a second channel, and potential difference between electrode 14 and the third electrode may be processed via a third channel.

Figure 3:
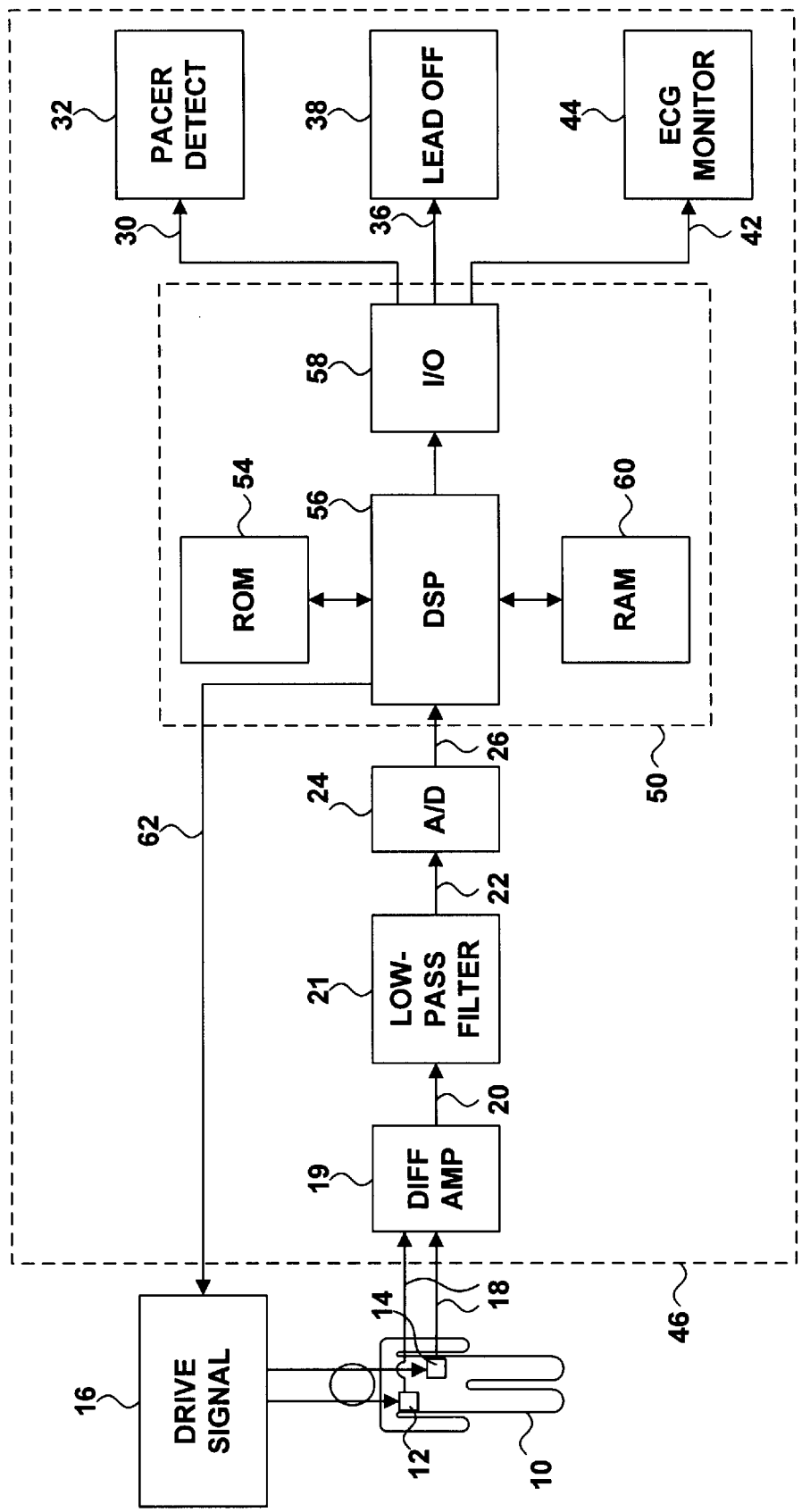
FIG. 3 is a functional block diagram illustrating an example implementation of the invention.

FIG. 3 shows the implementation of digital filters 28, 34 and 40 with software running on a single processor-implemented system 50. System 50 includes digital signal processor (DSP) 56. DSP 56 performs operations to filter digital signal 26 into signals 30, 36 and 42. In addition to digital filtering, DSP 56 also may control 62 drive signal 16. Instructions executed by DSP 56 may be supplied by read-only memory (ROM) 54 or random access memory (RAM) 60. The parameters of the digital filtering, such as bandwidth frequencies, can be modified by changing the instructions stored in RAM 60.

DSP 56 performs the digital filtering of digital filters 28, 34 and 40 simultaneously. The three software filters operate sequentially at the same rate. A single hardware element runs the three software filters, and it is not necessary to have separate hardware for each filter or each signal 30, 36 or 42. DSP 56 achieves digital filtering by performing mathematical operations to digital signal 26 to extract the frequency components of interest.

The results of digital filtering are passed to input/output (I/O) device 58, which supplies pacemaker signal 30 to pacer detection system 32, lead off signal 36 to lead off detector 38, and ECG signal 42 to ECG monitor 44. I/O device 58 may include a demultiplexer to supply signals 30, 36 and 42 to the respective instruments 32, 38 and 44. Alternatively, separate I/O devices may receive a signal from DSP 56, each I/O device supplying a signal to instruments 32, 38 and 44.

Figure 4:
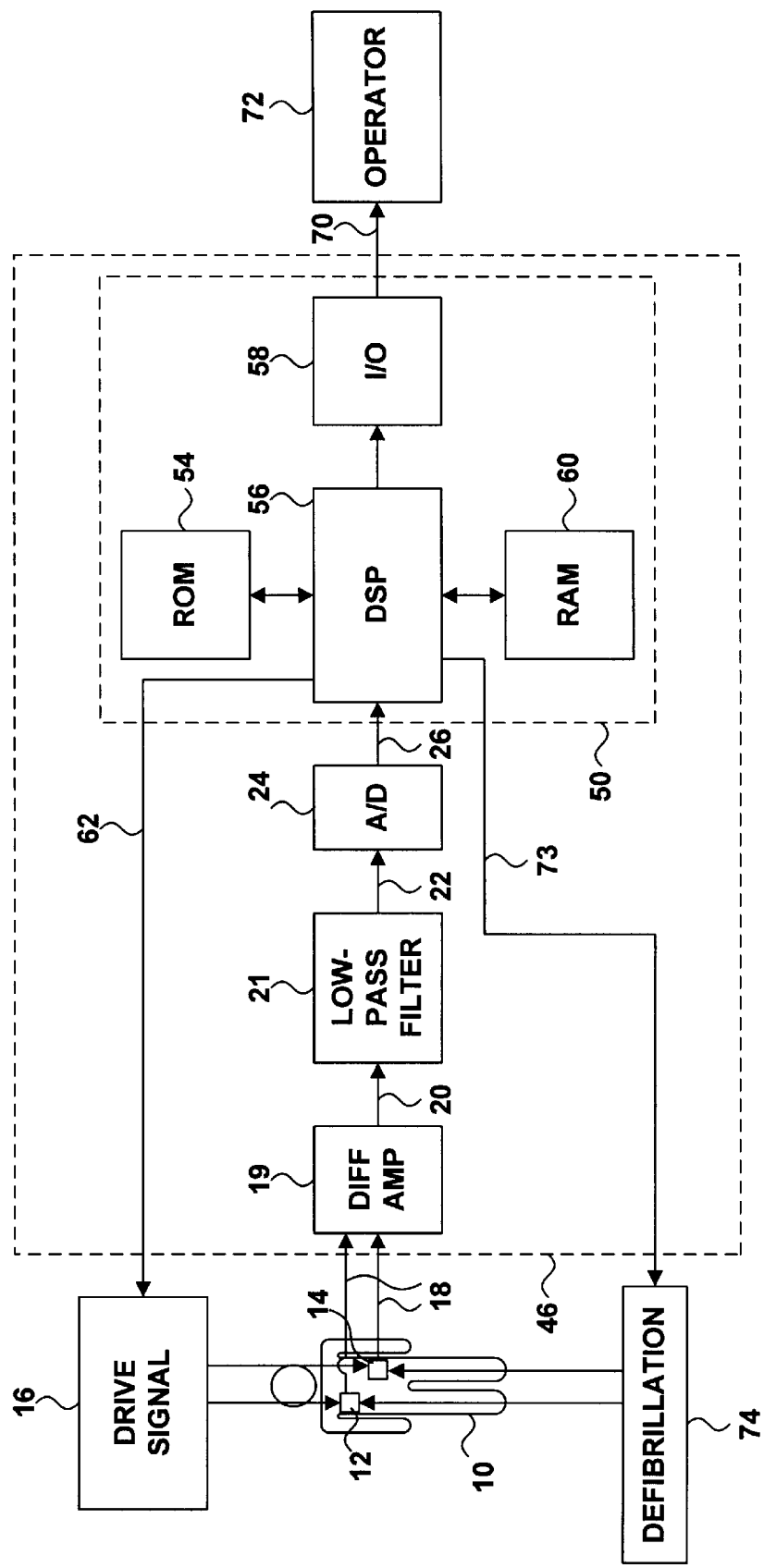
FIG. 4 is a functional block diagram illustrating an example implementation of the invention in conjunction with a defibrillator.

FIG. 4 depicts an alternate implementation of the invention. In this implementation, DSP 56 performs the functions of pacer detection system 32, lead off detector 38, and ECG monitor 44. In other words, DSP 56 not only performs digital filtering of digital signal 26, DSP 56 also analyzes the signals that result from the digital filtering. In particular, DSP 56 analyses the rate and rhythm of the heart, DSP 56 identifies the presence and timing of a pacemaker and DSP 56 detects poor electrical connections.

DSP 56 may further control a device such as defibrillator circuitry 74 as a function of the analysis. Upon detection of a shockable fibrillation, for example, DSP 56 may generate a control signal 73 to defibrillator circuitry 74, causing defibrillator circuitry 74 to store energy for the shock and to deliver the shock to patient 10 via electrodes 12 and 14. In addition, DSP 56 may notify operator 72 of the status of patient 10 or of the impending shock via I/O device 58. I/O device 58 may be embodied as a display screen, for example, or a voice prompt or an audible alarm.

In the embodiments depicted in FIGS. 1–4, patient 10 may be electrically isolated from DSP 56. Patient 10 may also be electrically isolated from the power supply that provides power to the active components shown in FIGS. 1–4. Patient 10 may be electrically isolated by transformers (not shown in FIGS. 1–4). Electrical isolation may also be optical. Digital signal 26, for example, may be encoded as an optical signal and may be transmitted with an optical coupling. Electrical isolation protects the safety of patient 10, and also protects DSP 56 in the event electrodes 12 and 14 are used to deliver a high-voltage defibrillation shock to patient 10.

Figure 5:
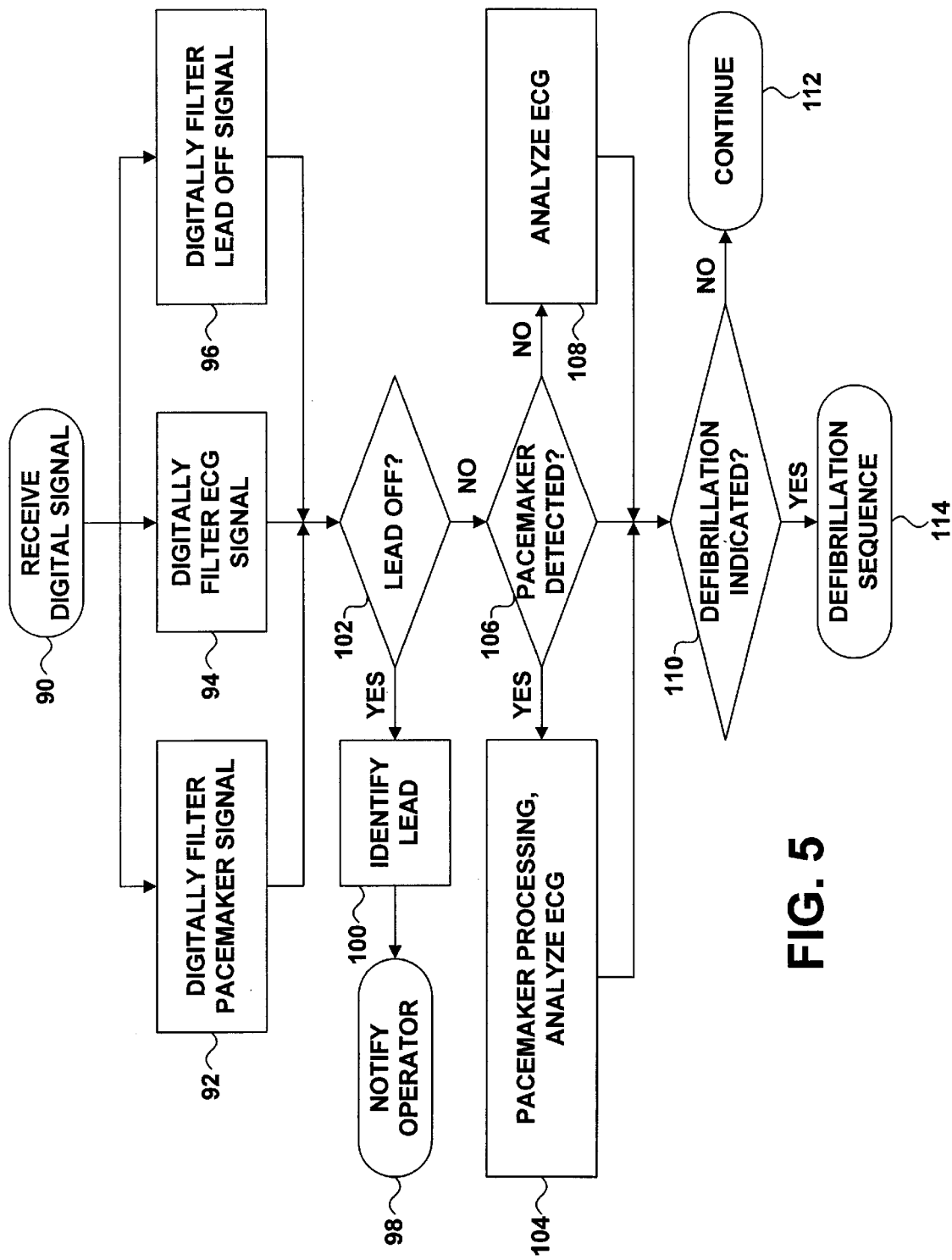
FIG. 5 is a flow diagram illustrating an embodiment of the invention.

FIG. 5 is a flow diagram showing a further embodiment of the invention. Upon receiving digital signal 26 (90), DSP 56 digitally filters digital signal 26 into pacemaker signal component 30 (92), ECG signal component 42 (94) and lead off signal component 36 (96). Digital filtering operations (92, 94, 96) are performed simultaneously.

In the exemplary techniques shown in FIG. 5, it is assumed that DSP 56 analyzes signals 30, 36 and 42, as shown in the implementation depicted in FIG. 4. The techniques shown in FIG. 5 may also be applied to implementations that use a dedicated signal analyzer 32, 38 or 44 for each signal component 30, 36 or 42, as shown in FIG. 3.

A poor quality signal may be detected by analysis of lead off signal 36 (102). As described above, more than two electrodes may be applied to patient 10. DSP 56 may identify which electrode or electrodes is improperly connected (100), and notify the operator 72 to correct the condition (98). In some cases, an improperly connected electrode may be identified by analyzing the lead off signal on each channel and determining which channel demonstrates a poor quality of the connection. Other techniques for identifying an improperly connected electrode may be employed as well.

DSP 56 analyzes pacemaker signal component 30 to determine whether patient 10 has an operating pacemaker (106). When patient 10 has a pacemaker, pacemaker signal component 30 includes high-frequency spikes. In such a case, DSP 56 may perform processing operations such as including the timing of pacing pulses the analysis of ECG signal 42 (104). DSP 56 may perform other processing operations as well, such as notifying operator 72 of the presence of a pacemaker, or displaying the spikes on a display screen or other I/O device 58.

When pacemaker signal component 30 is free from high-frequency spikes, DSP 56 evaluates ECG signal 42 without regard to pacing (108). When the evaluation of ECG signal 42 by DSP 56 indicates that a defibrillation shock is indicated (110), DSP 56 commences the defibrillation sequence (114). The defibrillation sequence may include generating signal 73 to control defibrillator circuitry 74, storing energy for a defibrillation shock and delivering the shock. When no defibrillation shock is indicated, DSP 56 may monitor digital signal 26 or may notify operator 72 via I/O device 58 that patient 10 has normal heart rhythm, or may perform some other action (112).

There are several advantages to the techniques described above. In contrast to conventional filtering circuits that use RLC elements, digital filters 28, 34 and 40 consume far less space and add less weight to signal processor 46 than RLC elements. A savings of space and weight is especially useful in a portable device such as an AED. Digital filters are also generally more reliable than an analog filter, and are less susceptible to factors such as temperature changes. In addition, a high-order digital filter may be inexpensive and is easily realized. Parameters such as cut-off frequencies can be modified by changing the instructions stored in RAM 60, without rewiring the circuit.

Various embodiments of the invention have been described. These embodiments are illustrative of the practice of the invention. Various modifications may be made without departing from the scope of the claims. For example, the invention has been described in the context of a defibrillator such as an AED, but the invention may be applied in other contexts as well. The invention may be implemented in a hospital emergency room, for example, and need not be coupled to a defibrillator.

Furthermore, the invention is not limited to the particular signals described above. The techniques of the invention may be applied to other signals from a patient that may be conducted by electrodes. Signals such as respiration signals and telemetry signals from a pacemaker or other implanted device may be conducted by electrodes in contact with the patient's skin.

In addition, various components in the described embodiments may be modified. Anti-aliasing filter 21, for example, may comprise a band-pass filter that eliminates high-frequency components and some low-frequency components. The multiple channel example of FIG. 2 may include separate A/D converters for each channel. These and other embodiments are within the scope of the following claims.

What is claimed is:

1. A device comprising:
    a first digital filter that receives a digital signal representative of a signal from a body and generates a pacemaker signal as a function of pacing pulses supplied by a pace maker; and
    a second digital filter that receives the digital signal and generates an electrocardiogram signal.

2. The device of 1, wherein the first digital filter passes frequency components above 300 Hz.

3. The device of claim 1, the second digital filter passes frequencies below 150 Hz.

4. The device of claim 1, further comprising a third digit filter that receives the digital signal and generates a signal indicative of the quality of the electrical connection of an electrode to the body.

5. The device of claim 4, wherein the third digital filter passes frequencies of 300 Hz.

6. The device of claim 1, further comprising:
   an anti-aliasing filter that receives an analog signal from the body and generates a filtered analog signal; and
   an analog-to-digital converter that receives the filtered analog signal and generates the digital signal.

7. The device of claim 6, further comprising:
   a first electrode in contact with the body;
   a second electrode in contact with the body; and
   a difference amplifier that supplies the analog signal to the anti-aliasing filter as a function of the potential difference between the first electrode and the second electrode.

8. The device of claim 7, further comprising:
   a third electrode in contact with the body;
   a fourth electrode in contact with the body; and
   a second difference amplifier that supplies a second analog signal to a second anti-aliasing filter as a function of the potential difference between the third electrode and the fourth electrode.

9. The device of claim 1, further comprising an analog-to-digital converter that receives a filtered signal and supplies the digital signal to the first digital filter and the second digital filter.

10. The device of claim 1, further comprising a processing system that includes the first digital filter and the second digital filter.

11. The device of claim 10, the processing system further comprising a digital signal processor that performs the functions of the first digital filter and the second digital filter.

12. The device of claim 1, further comprising a defibrillator that delivers a shock to the body as a function of the electrocardiogram signal.

13. A method comprising:
   digitally filtering an electrical signal representative of a signal from a body to generate a pacemaker signal as a function of pacing pulses supplied by a pacemaker; and
   digitally filtering the electrical signal to generate an electrocardiogram signal.

14. The method of claim 13, further comprising digitally filtering the electrical signal to generate a signal indicative of the quality of the electrical connection of an electrode to the body.

15. The method of claim 14, further comprising analyzing the electrocardiogram signal.

16. The method of claim 15, further comprising commencing a defibrillation sequence as a function of the analysis.

17. The method of claim 13, further comprising converting the electrical signal to a digital signal.

18. A device comprising:
   an analog-to-digital converter that receives an electrical signal from a body and generates a digital signal; and
   a processor that receives the digital signal and that digitally filters the digital signal to generate a pacemaker signal as a function of pacing pulses supplied by a pacemaker and digitally filters the digital signal to monitor an electrocardiogram signal.

19. The device of claim 18, further comprising an anti-aliasing filter that receives the electrical signal from the body and supplies a filtered electrical signal to the analog-to-digital converter.

20. The device of claim 19, further comprising:
   a first electrode in contact with the body;
   a second electrode in contact with the body; and
   a difference amplifier that supplies the electrical signal to the anti-aliasing filter as a function of the potential difference between the first electrode and the second electrode.

21. The device of claim 20, further comprising:
   a third electrode in contact with the body;
   a fourth electrode in contact with the body; and
   a second difference amplifier that supplies a second electrical signal to a second anti-aliasing filter as a function of the potential difference between the third electrode and the fourth electrode.

22. The device of claim 18, wherein the processor further digitally filters the digital signal to monitor the quality of an electrical connection of an electrode to the body.

23. The device of claim 18, further comprising an optical coupling that conveys the digital signal from the analog-to-digital converter to the processor.

24. The device of claim 18, further comprising a defibrillator that delivers a shock to the body as a function of the electrocardiogram signal.

25. A method comprising:
   digitally filtering an electrical signal representative of a signal from a body to generate an electrocardiogram signal; and
   simultaneously digitally filtering the electrical signal to generate a second patient signal.

26. The method of claim 25, wherein the second patient signal is one of a pacemaker signal as a function of pacing pulses supplied by a pacemaker, a signal indicative of the quality of the electrical connection of an electrode to the body, a signal as a function of respiration and a signal as a function of telemetry signals supplied by a device implanted in the body.

* * * * *

UNITED STATES PATENT AND TRADEMARK OFFICE
CERTIFICATE OF CORRECTION

PATENT NO. : 6,823,209 B2
DATED : November 23, 2004
INVENTOR(S) : Dana J. Olson et al.

It is certified that error appears in the above-identified patent and that said Letters Patent is hereby corrected as shown below:

<u>Column 6,</u>
Line 66, "digit" should read -- digital --.

Signed and Sealed this

Ninth Day of May, 2006

JON W. DUDAS
*Director of the United States Patent and Trademark Office*